(12) United States Patent
Callister et al.

(10) Patent No.: US 9,713,549 B2
(45) Date of Patent: Jul. 25, 2017

(54) CONTRACEPTIVE WITH PERMEABLE AND IMPERMEABLE COMPONENTS

(75) Inventors: Jeffrey P. Callister, Redwood City, CA (US); William S. Tremulis, Redwood City, CA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 2032 days.

(21) Appl. No.: 11/047,319

(22) Filed: Jan. 31, 2005

(65) Prior Publication Data

US 2005/0192616 A1 Sep. 1, 2005

Related U.S. Application Data

(60) Provisional application No. 60/541,821, filed on Feb. 2, 2004.

(51) Int. Cl.
| | | |
|---|---|---|
| *A61F 6/22* | (2006.01) | |
| *A61B 17/12* | (2006.01) | |
| *A61F 6/20* | (2006.01) | |
| *A61B 17/00* | (2006.01) | |

(52) U.S. Cl.
CPC .......... *A61F 6/22* (2013.01); *A61B 17/12022* (2013.01); *A61B 17/12136* (2013.01); *A61B 17/12163* (2013.01); *A61B 17/12172* (2013.01); *A61B 17/12177* (2013.01); *A61B 17/12181* (2013.01); *A61F 6/225* (2013.01); *A61B 17/0057* (2013.01); *A61B 17/1215* (2013.01); *A61B 2017/12054* (2013.01); *A61B 2017/12095* (2013.01); *A61F 6/20* (2013.01)

(58) Field of Classification Search
CPC ........ A61B 17/12022; A61B 17/12136; A61B 17/12163; A61B 17/12177; A61B 17/12036; A61B 17/1204; A61B 17/12181; A61F 6/225; A61F 6/20; A61F 6/22; A61F 6/146

USPC .......... 606/213, 151, 157–158, 198
See application file for complete search history.

(56) References Cited

U.S. PATENT DOCUMENTS

| | | |
|---|---|---|
| 3,334,629 A | 8/1967 | Cohn |
| 3,687,129 A | 8/1972 | Nuwayser |
| 3,815,578 A | 6/1974 | Bucalo |
| 3,834,394 A | 9/1974 | Hunter et al. |
| 3,855,996 A | 12/1974 | Bolduc |

(Continued)

FOREIGN PATENT DOCUMENTS

| | | |
|---|---|---|
| AU | 707047 | 7/1999 |
| AU | 739429 | 10/2001 |

(Continued)

OTHER PUBLICATIONS

Notice of Opposition (Australian Patent Application No. 769576) (Apr. 27, 2004).

(Continued)

*Primary Examiner* — Christopher L Templeton
*Assistant Examiner* — Lucas Paez

(57) ABSTRACT

An device for occluding a body lumen such as a reproductive lumen which includes an occluding component having an impervious barrier to provide initial occlusion of the body lumen and a permeable body to facilitate tissue ingrowth which provides long term occlusion of the body lumen. The device and the method of using the device is particularly suitable for contraception.

10 Claims, 9 Drawing Sheets

(56) References Cited

U.S. PATENT DOCUMENTS

| | | | |
|---|---|---|---|
| 3,865,108 A | 2/1975 | Hartop | |
| 3,868,956 A | 3/1975 | Alfidi et al. | |
| 3,991,760 A | 11/1976 | Drobish et al. | |
| 4,052,754 A | 10/1977 | Homsy | |
| 4,140,126 A | 2/1979 | Choudhury | |
| 4,185,618 A | 1/1980 | Corey | |
| 4,246,896 A | 1/1981 | Horne et al. | |
| 4,279,252 A | 7/1981 | Martin | |
| 4,311,146 A | 1/1982 | Wonder | |
| 4,441,495 A | 4/1984 | Hicswa | |
| 4,503,569 A | 3/1985 | Dotter | |
| 4,562,596 A | 1/1986 | Kornberg | |
| 4,579,110 A | 4/1986 | Hamou | |
| 4,595,000 A | 6/1986 | Hamou | |
| 4,606,336 A | 8/1986 | Zeluff | |
| 4,638,803 A | 1/1987 | Rand | |
| 4,657,000 A | 4/1987 | Hepburn | |
| 4,688,553 A | 8/1987 | Metals | |
| 4,700,701 A | 10/1987 | Montaldi | |
| 4,705,517 A * | 11/1987 | DiPisa, Jr. | 606/158 |
| 4,733,665 A | 3/1988 | Palmaz | |
| 4,787,899 A | 11/1988 | Lazarus | |
| 4,869,268 A | 9/1989 | Yoon | |
| 4,964,850 A | 10/1990 | Bouton et al. | |
| 4,969,458 A | 11/1990 | Wiktor | |
| 4,994,069 A | 2/1991 | Ritchart et al. | |
| 5,104,399 A | 4/1992 | Lazarus | |
| 5,108,420 A | 4/1992 | Marks | |
| 5,147,370 A | 9/1992 | McNamara et al. | |
| 5,163,958 A | 11/1992 | Pinchuk | |
| 5,167,614 A | 12/1992 | Tessmann et al. | |
| 5,176,692 A | 1/1993 | Wilk et al. | |
| 5,190,546 A | 3/1993 | Jervis | |
| 5,192,301 A | 3/1993 | Kamiya et al. | |
| 5,197,978 A | 3/1993 | Hess | |
| 5,226,911 A | 7/1993 | Chee et al. | |
| 5,267,945 A | 12/1993 | Doctor et al. | |
| 5,275,622 A | 1/1994 | Lazarus et al. | |
| 5,303,719 A | 4/1994 | Wilk et al. | |
| 5,354,295 A | 10/1994 | Guglielmi et al. | |
| 5,366,472 A | 11/1994 | Hillstead | |
| 5,370,657 A | 12/1994 | Irie | |
| 5,382,259 A | 1/1995 | Phelps et al. | |
| 5,382,261 A | 1/1995 | Palmaz | |
| 5,423,849 A | 6/1995 | Engelson et al. | |
| 5,433,217 A | 7/1995 | Pianetti et al. | |
| 5,443,500 A | 8/1995 | Sigwart | |
| 5,456,713 A | 10/1995 | Chuter | |
| 5,474,089 A | 12/1995 | Waynant | |
| 5,489,295 A | 2/1996 | Piplani et al. | |
| 5,499,995 A * | 3/1996 | Teirstein | A61B 17/12022 606/192 |
| 5,507,811 A | 4/1996 | Koike et al. | |
| 5,512,051 A | 4/1996 | Wang et al. | |
| 5,514,176 A | 5/1996 | Bosley, Jr. | |
| 5,545,210 A | 8/1996 | Hess et al. | |
| 5,601,593 A | 2/1997 | Freitag | |
| 5,601,600 A | 2/1997 | Ton | |
| 5,643,311 A | 7/1997 | Smith et al. | |
| 5,656,036 A | 8/1997 | Palmaz | |
| 5,669,933 A | 9/1997 | Simon et al. | |
| 5,766,203 A | 6/1998 | Imran | |
| 5,836,968 A | 11/1998 | Simon et al. | |
| 5,919,202 A | 7/1999 | Yoon et al. | |
| 5,935,137 A | 8/1999 | Saadat et al. | |
| 6,090,063 A | 7/2000 | Makower et al. | |
| 6,096,052 A | 8/2000 | Callister | |
| 6,145,505 A | 11/2000 | Nikolchev et al. | |
| 6,176,240 B1 | 1/2001 | Nikolchev et al. | |
| 6,187,027 B1 | 2/2001 | Mariant et al. | |
| 6,270,495 B1 | 8/2001 | Palermo | |
| 6,270,515 B1 * | 8/2001 | Linden et al. | 606/213 |
| 6,312,446 B1 * | 11/2001 | Huebsch et al. | 606/213 |
| 6,378,524 B1 | 4/2002 | Jones | |
| 6,432,116 B1 * | 8/2002 | Callister et al. | 606/157 |
| 6,517,559 B1 | 2/2003 | O'Connell | |
| 6,526,979 B1 | 3/2003 | Nikolchev et al. | |
| 6,565,557 B1 | 5/2003 | Sporri et al. | |
| 6,634,361 B1 | 10/2003 | Nikolchev et al. | |
| 6,638,293 B1 * | 10/2003 | Makower et al. | 606/200 |
| 6,679,266 B2 | 1/2004 | Nikolchev et al. | |
| 6,684,884 B2 | 2/2004 | Nikolchev et al. | |
| 6,705,323 B1 | 3/2004 | Nikolchev et al. | |
| 6,706,054 B2 | 3/2004 | Wessman et al. | |
| 6,709,667 B1 | 3/2004 | Lowe et al. | |
| 6,716,238 B2 | 4/2004 | Elliott | |
| 6,763,833 B1 | 7/2004 | Khera et al. | |
| 6,871,650 B1 | 3/2005 | Nikolchev et al. | |
| 6,966,892 B2 | 11/2005 | Gandhi et al. | |
| 2002/0013589 A1 | 1/2002 | Callister et al. | |
| 2002/0020417 A1 | 2/2002 | Nikolchev et al. | |
| 2002/0029051 A1 * | 3/2002 | Callister et al. | 606/157 |
| 2003/0066533 A1 | 4/2003 | Loy | |
| 2004/0073242 A1 * | 4/2004 | Chanduszko | 606/157 |
| 2004/0079377 A1 | 4/2004 | Nikolchev et al. | |
| 2004/0127918 A1 | 7/2004 | Nikolchev et al. | |
| 2004/0159324 A1 | 8/2004 | Nikolchev et al. | |
| 2004/0163650 A1 | 8/2004 | Lowe et al. | |
| 2004/0163651 A1 | 8/2004 | Nikolchev et al. | |
| 2004/0206358 A1 | 10/2004 | Nikolchev et al. | |
| 2004/0211429 A1 | 10/2004 | Nikolchev et al. | |
| 2005/0085844 A1 | 4/2005 | Tremulis et al. | |
| 2005/0107867 A1 | 5/2005 | Teheri | |

FOREIGN PATENT DOCUMENTS

| | | |
|---|---|---|
| DE | 3038928 A1 | 4/1982 |
| EP | 0 105 669 | 4/1984 |
| EP | 1 199 049 | 4/2002 |
| WO | WO 90/09158 | 8/1990 |
| WO | WO 93/06884 | 4/1993 |
| WO | WO 94/24944 | 11/1994 |
| WO | WO94/26175 | 11/1994 |
| WO | WO 96/40024 | 12/1996 |
| WO | WO97/27893 | 8/1997 |
| WO | WO 98/26737 | 6/1998 |
| WO | WO 99/15116 | 4/1999 |
| WO | WO01/13833 | 3/2001 |

OTHER PUBLICATIONS

Statement of Grounds and Particulars (Australian Patent Application No. 769576) (Aug. 5, 2004).

Declaration of Kathryn Tunsdall (Australian Patent Application No. 769576) (Oct. 19, 2004).

Declaration of Julian Nikolchev (Australian Patent Application No. 769576) (Nov. 5, 2004).

Declaration of Dr. Gabor Thomas Kovacs (Australian Patent Application No. 769576) (Nov. 18, 2004).

Declaration of Dr. John F. Kerin (Australian Patent Application No. 769576) (Nov. 19, 2004).

Second Declaration of Dr. John F. Kerin (Australian Patent Application No. 769576) (Nov. 19, 2004).

T. Schmitz-Rode, MD, et al., "Experimental nonsurgical female sterilization: transcervical implantation of microspindles in fallopian tubes," Journal of Vascular and Interventional Radiology, vol. 5 (No. 6), pp. 905-910, (Nov.-Dec. 1994).

A. Thurmond, MD, "Transcervical fallopian tube catheterization," Seminars in Interventional Radiology, vol. 9 (No. 2), pp. 80-86, (Jun. 1992).

T. Schmitz-Rode, MD, et al., "Self-expandable spindle for transcatheter vascular occlusion: in vivo experiments," Radiology, vol. 188 (No. 1), pp. 95-100, (Jul. 1993).

Docket for Civil Action No. C 02 1968 MHP (U.S. District Court for the Northern District of California).

Docket for Civil Action No. C 02 3884 MHP (U.S. District Court for the Northern District of California).

First Amended complain For (1) Declaratory Judgment of Patent Non-Infringement, Invalidity and Unenforceability; (2) False Advertising Under 15 USC §1125(A); (3) Trade Libel; (4) Unfair

(56) References Cited

OTHER PUBLICATIONS

Competition Under Common Law and Cal. B&P §17200 Et Seq.; (5) Unjust Enrichment; and (6) Constructive Trust Demand for Jury Trial, Jun. 13, 2002.
Ovion's Request, Pursuant to Civil Local Rule 7-10(b), For Leave To File A Motion To Dismiss Before The Initial Case Management Conference.
Conceptus' Amended Answer to Ovion's Complaint, Affirmative Defenses and Counterclaims, Sep. 26, 2002.
Ovion's Reply To Amended Counterclaims Of Conceptus, Oct. 25, 2002.
First Amended Complaint For Willful Patent Infringement, Fraud And Misrepresentation, Misappropriation, Unjust Enrichment, Unfair Business Practices, Trade Libel, Slander Of Title, Monopolization, Attempt To Monopolize And Sham Litigation, Aug. 25, 2003.
Conceptus' Second Amended Answer, Affirmative Defenses And Counterclaims For: (1) Declaratory Judgment Of Non-Infringement; (2) Declaratory Judgment Of Unenforceability; (3) Declaratory Judgment Of Invalidity; (4) Correction Of Inventorship of '052 Patent Under 35 USC §256; (5) Correction of Inventorship Of '116 Patent Under 35 USC §256; (6) Fraud And Deceit; (7) Trade Libel; (8) Slander Per Se; (9) Libel; (10) Unfair Competition; And, (11) Slander Of Title, Jul. 2, 2003.
Joint Claim Construction and Prehearing Statement Pursuant To Patent Local Rule 4-3, Aug. 6, 2003.
Stipulation And Order Of Dismissal, Nov. 13, 2003.
Ovion's Response to Conceptus' Interrogatories Nos. 2-4, 6-10, and 12-13, Nov. 1, 2002.
Ovion's Corrected Disclosure of Asserted Claims and Preliminary Infringement Contentions, Nov. 19, 2002.
Ovion's Corrected Supplemental Statement Regarding Dates of Invention, Nov. 19, 2002.
Ovion's Second Supplemental Statement Regarding Dates of Invention, Dec. 20, 2002.
Letter from L. Hansen to Judge Patel, Jul. 28, 2003.
Letter from L. Hansen to Judge Patel, Aug. 5, 2003.
Letter from L. Hansen to Judge Patel, Aug. 7, 2003.
Letter from J. Benassi to Judge with declarations of E. Brann and A. Khera, Aug. 8, 2003.
Letter from E. Brann to Judge Patel with signed declaration of A. Khera, Aug. 13, 2003.
Letter from L. Hansen to Judge Patel, Aug. 15, 2003.
Letter from L. Hansen to Judge Patel, enclosing for submission on behalf of Ovion its First Amended Complaint, Aug. 25, 2003.
Letter from J. Benassi to Judge Patel, Aug. 28, 2003.
Conceptus' Motion for Summary Judgment of Invalidity of the Asserted '116 patent Claims in View of Conceptus, Inc.'s '979 Patent, Oct. 6, 2003.
Ovion's Motion To Change Time for Conceptus' Inappropriate Summary Judgment Motions, Oct. 10, 2003.
Declaration of Leland G. Hansen In Support Of Ovion's Motion To Change Time, with Exhibits 1-8, Oct. 10, 2003.
Plaintiff Conceptus, Inc.'s Response to Defendant Ovion, Inc.' First Set of Interrogatories Nos. 1-6, Nov. 1, 2002.
Plaintiff Conceptus Inc.'s Initial Disclosure Pursuant to Fed.R.Civ. P. 26(a)(1), Nov. 1, 2002.
Plaintiff Conceptus, Inc.'s Supplemental Written Statement Concerning Dates of Invention, Dec. 20, 2002.
Plaintiff Conceptus, Inc.'s Supplemental Response to Defendant Ovion, Inc.'s Interrogatory No. 1, Dec. 20, 2002.
Plaintiff Conceptus Inc.'s Corrected Supplemental Response to Defendant Ovion, Inc.'s Interrogatory No. 1, Jan. 6, 2003.
Plaintiff Conceptus, Inc.'s Corrected Supplemental Written Statement Concerning Dates of Invention, Jan. 6, 2003.
Conceptus, Inc.'s Preliminary Invalidity Contentions, Apr. 30, 2003.
International Search Report for PCT/US2005/003185, mailed May 2, 2005.
Written Opinion of the International Searching Authority for PCT/US2005/003185, mailed May 2, 2005.
International Search Report for PCT/US2005/003310, mailed May 2, 2005.
Written Opinion of the International Searching Authority for PCT/US2005/003310, mailed May 2, 2005.
Written Opinion of the International Searching Authority for PCT/US2003/41275, mailed Apr. 25, 2005.
Declaration of Steven Bachich in Support of Conceptus' Motion for Summary Judgment of Invalidity in View of Conceptus, Incs;s '979 Patent (Oct. 5, 2003).
Defendants' Request, Pursuant to Civil Local Rule 7-10(b), For Leave to File a Motion to Dismiss Before the Initial Case Management Conference (Jul. 22, 2002).
Ovion's Motion to Change Time for Conceptus' Inappropriate Summary Judgement Motions, Oct. 10, 2003.
PCT International Preliminary Report on Patentability for PCT/US2005/003310 mailed Aug. 17, 2006.
PCT International Preliminary Report on Patentability for PCT/US2005/003185 mailed Aug. 17, 2006.
Curry, M.R., et al., "Surface Area and Volume Measurements for Ram and Human Spermatozoa," Biology of Reproduction, vol. 55, 1996, pp. 1325-1332.
"Mammal erythrocyte sizes," Animal Genome Size Database, last modified by T. Ryan Gregory on Feb. 3, 2004, accessed at http://genomesize.com/cellsize/mammals.htm on May 26, 2011, 18 pages.
"sperm." Encyclopaedia Britannica. Encyclopaedia Britannica Online. Encyclopaedia Britannica, 2011, accessed at http://www.britannica.com/EBchecked/topic/559354/sperm on May 26, 2011.
Vander, Arthur J., et al., "Human Physiology—The Mechanisms of Body Function" 2nd edition, McGraw-Hill Book Company, 1975, p. 299.

\* cited by examiner

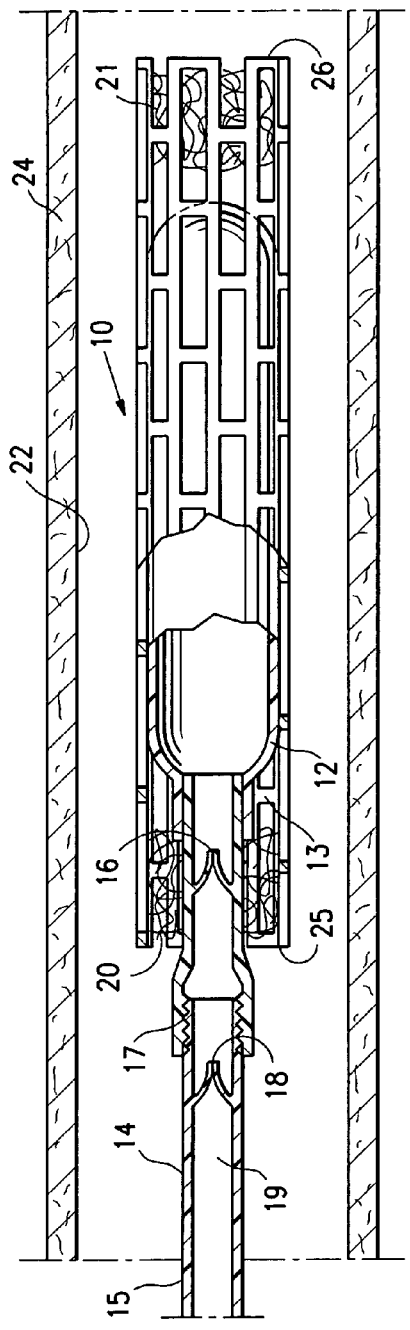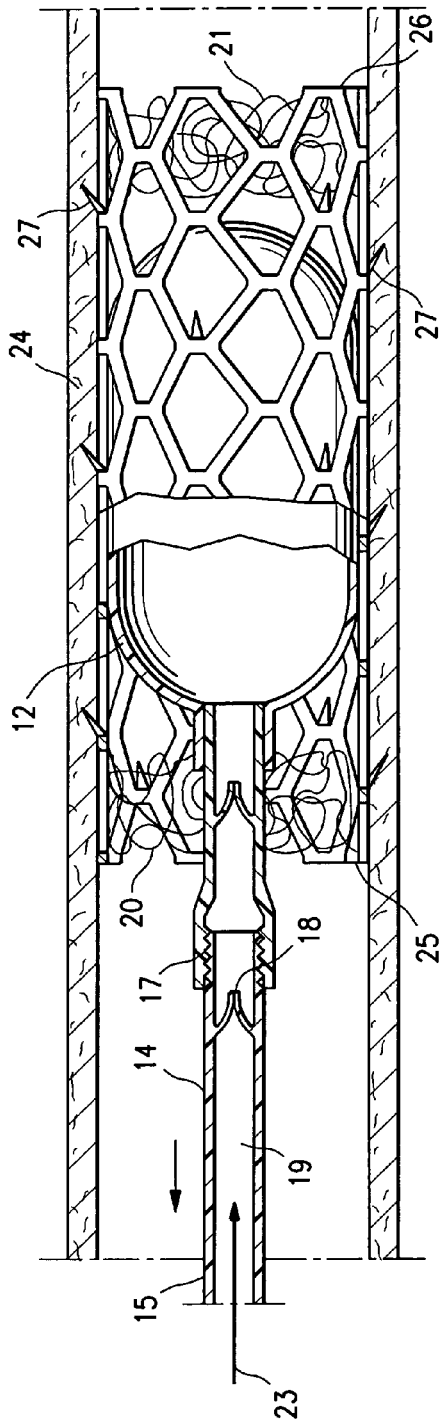
FIG. 1A
FIG. 1B

US 9,713,549 B2

CONTRACEPTIVE WITH PERMEABLE AND IMPERMEABLE COMPONENTS

RELATED APPLICATIONS

This application claims priority to U.S. Provisional Application No. 60/541,821 filed Feb. 2, 2004, which is incorporated herein by reference in its entirety.

BACKGROUND OF THE INVENTION

This invention generally relates to the field of occluding devices, delivery systems for such devices and the method of using such devices and systems in the occlusion of body passageways. The invention is particularly useful for the occluding reproductive lumens such as a female patient's fallopian tubes or a male patient's vas deferens to affect contraception.

Conventional contraceptive strategies generally fall within three categories: physical barriers, drugs and surgery. While each have certain advantages, they also suffer from various drawbacks. Barriers such as condoms and diaphragms are subject to failure due to breakage, displacement and misplacement. Drug strategies, such as the pill and Norplant™, which rely on artificially controlling hormone levels, suffer from known and unknown side-effects from prolonged use. Surgical procedures, such as tubal ligation and vasectomy, are very effective, but involve the costs and attendant risks of surgery, and are frequently not reversible.

Recently, minimally invasive treatments have be proposed which deploy occluding stent-like devices within reproductive lumens, e.g. the fallopian tubes or vas deferens, as a contraceptive alternative to tubal ligation or vasectomy. However, placing a stent or similar occluding device may not create sufficient or permanent obstruction of the reproductive lumen depending on the nature of the obstructive device. For example, the obstructive device may be too small to provide complete obstruction of the reproductive lumen, or the device may be permeable to cell movement. An occluding device placed in a reproductive lumen, for example, may not securely seal against the luminal walls, or may initially allow egg cells or sperm cells to pass through the device until tissue growth completes the occlusion of the reproductive lumen and thus allow pregnancy to occur. Additionally, the occluding device might create an initial obstruction sufficient to prevent the passage of an egg but allow sperm cells to pass through or by the occluding device, fertilizing an egg upstream of the obstruction and resulting in an ectopic pregnancy.

The use of an occluding contraceptive or sterilization device, particularly with mesh or fibrous material to promote tissue ingrowth, has been proposed (See for example U.S. Pat. Nos. 6,096,052 and 6,432,116). However, with these devices there is an initial period (several weeks to several months) after deployment during which the patient is at risk for cell passage through the device that can result in pregnancy. In such situations it may be desirable to use a supplemental method of birth control until tissue ingrowth effectively occludes the fallopian tube. The same initial risks are found when occluding a male's vas deferens.

Even in situations in which complete obstruction has been achieved initially, the body lumen may recanalize. For example, an obstruction placed in a fallopian tube may create an initial blockage that obstructs passage of sperm or eggs. However, over time the walls of the tube may reconfigure to create a channel around the obstruction, effectively recanalizing the fallopian tube.

SUMMARY OF THE INVENTION

The present invention relates devices and methods for occluding a body lumen, particularly a reproductive body lumen such as a female patient's fallopian tube or a male patient's vas deferens, which effectively occludes the body lumen initially and over the long term.

Occluding devices which incorporate features of the invention generally have an expandable occluding component configured for deployment within the patient's body lumen such as a reproductive lumen. The occluding component has an impermeable barrier element secured thereto which is substantially impermeable to the passage of biological components such as cells, particularly reproductive cells such as eggs and sperm cells to provide an immediate barrier, i.e. at the time of deployment. The occluding component also has one or more permeable components that are secured to, disposed within or otherwise part of the occluding component to facilitate tissue growth that provides long term or permanent occlusion. Tissue growth can be into or onto the occluding component to at least partially occlude the reproductive lumen. Tissue growth may include epithelialization, scar formation, cell proliferation, or other cell growth or multiplication.

One occluding device embodying features of the invention has an occluding component in the form of a stent-like structure which has an impermeable barrier component to ensure initial occlusion of the body lumen and a permeable component to facilitate tissue ingrowth into or onto the stent-like structure of the occluding component for long term or permanent occlusion thereof.

In one embodiment, the impermeable barrier component is an inflatable and detachable balloon formed of impermeable material. The stent-like structure is mounted onto an impermeable, inflatable and detachable balloon of a delivery device such as a catheter. and the distal end of the delivery device is introduced into the body lumen and advanced therein until the detachable balloon is disposed in the location where the user desires to place the occluding device. The balloon is then inflated to the desired size, preferably to the diameter or a slightly larger dimension than the diameter of the body lumen. The expansion of the balloon expands the stent-like structure mounted on the balloon and against the wall of body lumen. After inflation, the shaft of the delivery catheter is disengaged from the detachable balloon portion of the delivery catheter and then withdrawn, leaving the stent-like structure in place against the walls of the body structure with the inflated, detached balloon disposed within the inner lumen of the stent-like occluding component. One or more permeable components such as fibrous mesh, a fiber bundle or a porous polymeric mass or plug are provided within the occluding component to facilitate tissue ingrowth and over time to create an effective and permanent occlusion of the body lumen.

A modification of the embodiment described above is to provide an impermeable diaphragm or membrane within the inner lumen of the stent-like occluding component or over one or more ends of the stent-like occluding component that seals the lumen of the stent when the stent-like structure is expanded against the walls of the body structure. The stent-like occluding component may be balloon expandable or self-expandable. A fibrous or otherwise porous mass or body, for example strands or bundles of biocompatible fibers or open cell biocompatible foam, may be provided within the stent-like structure as described above to facilitate tissue ingrowth.

A self-expanding occluding component may be formed of a superelastic metal such as NiTi which has been treated to have a stable austenite phase at body temperature and stress induced or stress maintained martensite phase. The occluding component may be in one, small diameter configuration for delivery in a suitable delivery catheter and expand upon discharge from the delivery catheter to a larger dimensioned second configuration within the body lumen. Alternatively, the occluding component may be formed of shape memory metallic material such as NiTi alloy which has a stable martensite phase at body temperature but which expands to a remembered larger diameter configuration when heated to transform the martensite to the austenite phase.

An expandable mass such as a plug on the interior of the occluding component may also to provide the expansion or augment natural or other expansion of the occluding component. The expandable mass may be the impermeable barrier component or the permeable component which facilitates tissue ingrowth.

Another occluding device embodying features of the invention is an occluding component comprising an expandable plug having a plurality of segments, at least one of which is an impermeable barrier component for initial occlusion of the body lumen and at least one of which is a permeable component configured to facilitate tissue ingrowth that provides a long term or permanent occlusion. The plug is configured to be compressible for delivery within a delivery sheath and to be expandable within the body lumen when discharged from the delivery sheath. The impermeable barrier segment may be an impermeable membrane or a closed cell mass or both. The permeable segment may be a fibrous or porous mass or both. The occluding component of this embodiment may have a stent-like attachment ring at one or both ends of the occluding device to secure the occluding component at least partially within the body lumen. The occluding component or attachment rings may be provided with anchoring elements such as hooks or barbs to secure the occluding component within the body lumen. The expanded occluding device provides an immediately effective occlusion of the body lumen, while tissue ingrowth over time provides a permanent and effective occlusion of the body lumen.

The occluding component may have the structure described in copending application Ser. No. 10/746,131, filed on Dec. 24, 2004, assigned to the present assignee which discloses an occluding component having one or more expanding spider-like elements. The impermeable barrier component is an impermeable membrane secured to the expanding legs of the spider-like element to provide initial occlusion of the body lumen. Fibrous or porous material may be secured to the expanding legs of the spider-like elements or to a central support shaft or spine connecting spider-like elements of the occluding component.

Other occluding components embodying features of the invention may comprise a plurality of expandable disks on a shaft in which at least one of the disks is an impermeable barrier component and at least one is a permeable component as described above.

Another occluding device has a stent-like occluding component with an enlarged bullet shaped impermeable barrier component on the leading end of the occluding component. One or more permeable components may be disposed in the interior of the occluding component.

The occluding component will generally be about 1 to about 5 mm, preferably about 2 to about 4 mm in transverse dimension in the expanded configuration and will generally be about 0.5 to about 8 cm, preferably about 1.5 to about 4 cm in length. While the description herein is focused on the use of only one occluding device, two or more occluding devices may be employed in a reproductive lumen.

The occluding devices and methods of using such occluding devices embodying features of the invention are effective both initially and over the long term in occluding the body lumen sufficiently to prevent the passage therethrough of undesirable biological elements, e.g. cells. The methods and devices are particularly beneficial for occluding reproductive lumens for contraceptive purposes. Although the occlusion of a patient's reproductive lumens are discussed herein in detail, it can be appreciated that the devices, methods and systems described herein can easily be adapted to occlude a patient's arteries or veins in a variety of situations, the nidus of an arterial-venous malformation, patent ductus arteriosis in infants, as well as arteries feeding blood to cancerous tumors.

These and other features of this invention will become more apparent in light of the detailed description of the invention and the exemplary drawings contained herein.

BRIEF DESCRIPTION OF THE DRAWINGS

FIG. 1A is an elevational view of an occluding device embodying features of the invention with a detachable, unexpanded balloon disposed within the inner lumen of the stent-like occluding component.

FIG. 1B is an elevational view of the invention depicted in FIG. 1A with the balloon inflated.

DETAILED DESCRIPTION OF THE INVENTION

Figure 1C:
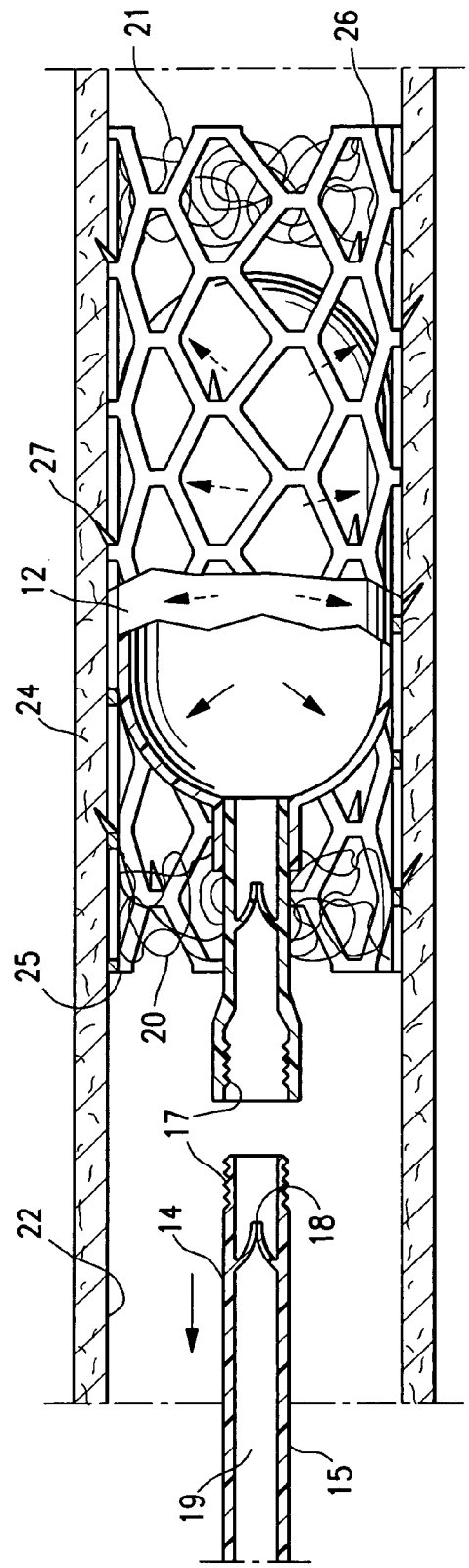
FIG. 1C is an elevational view of the inflated balloon in a detached configuration.

FIGS. 1A-1C depict an occluding device 10 embodying features of the invention which includes an expandable, stent-like occluding component 11 and an inflatable detachable balloon-like barrier component 12 contained within the inner lumen 13 of the stent-like occluding component. The detachable balloon-like barrier element 12 is releasably secured to the distal shaft portion 14 of delivery catheter 15. The inflatable balloon-like barrier 12 is located distal to a one-way valve 16 (e.g. a duck-billed valve as shown) which allows inflation fluid to be injected into the interior or the balloon like barrier, but prevents inflation fluid from flowing out of the balloon interior. A threaded connection 17 is provided between the balloon assembly and the distal shaft portion 14 of the delivery catheter 15 to detach the balloon-like barrier component 12 at the desired location. A second optional one-way valve 18 may be located proximal of the threaded connection 17 to act as a back flow valve within the inflation lumen 19 of the delivery catheter 15 to prevent body fluid from entering the inflation lumen after the balloon-like barrier element 12 has been detached.

The balloon-like barrier component 12 is formed of impermeable, biocompatible polymeric material. Suitable polymeric materials include polyethylene terephthalate (PET), nylon and polyesters such as Hytrel®. Other moderately-compliant to essentially non-compliant biocompatible polymeric materials are suitable. Biocompatible and bioresorbable materials such as polylactic acid, polyglycolic acid, polycaprolactone and blends and copolymers thereof are also suitable in some instances.

A plurality of fibrous permeable components 20 and 21 are provided within the stent-like occluding component 11 at each end thereof to facilitate tissue ingrowth therein. The permeable components may be a mass of fibrous material as shown, or a plug or mass of porous polymeric material.

The occluding member 10 is advanced to the desired location within the body lumen 22, such as a female patient's fallopian tube, with the stent-like occluding component 11 mounted on the balloon-like barrier element 12 in a non-inflated condition. Inflation fluid (indicated by the arrows 23 in FIG. 1B) is introduced through the catheter's inflation lumen 19 into the interior of the balloon-like barrier component 11 to inflate the barrier component within the stent-like occluding component 11 to expand the occluding component until it is in contact with the wall 24 of the body lumen 22. The inflation fluid may be saline, a biocompatible gas, or some other similar fluid or fluid like substance. The inflation fluid may be a liquid or foam that solidifies after inflation, so that the balloon is a relatively solid structure after inflation.

The balloon of the occluding component 11 will be inflated with sufficient pressure to press the stent like component 11 against the wall of the body lumen 22 and form a secure seal between the balloon and the body lumen wall, but not with sufficient force to rupture or otherwise damage the lumen or the balloon. The detachable distal shaft section 14 of the delivery catheter 15 is detached from the balloon assembly by rotating the shaft to unscrew the shaft section from the balloon section. After detaching the shaft 15 from the balloon, the back-flow valve 18 prevents fluid in the body lumen from traveling back up the inner lumen 19 of the delivery catheter 15. The one-way valve 16 adjacent the balloon prevents loss of inflation fluid and ensures that the balloon remains in the inflated condition.

The balloon of the impermeable barrier component 12 is made of a material which is impermeable to preselected biological elements in order to seal the body lumen and prevent the passage of such biological elements. As used herein, "impermeable" means impermeable to the extent and appropriate for the purpose. For example, a barrier for contraceptive purposes in a reproductive lumen such as a fallopian tube or vas deferens is impermeable if, when placed across the reproductive lumen, it will block the passage of sperm cells or an egg through the reproductive lumen. The barrier need not be air tight, fluid tight (indeed the ability to pass some fluid might be desirable) and may even allow the passage and ingrowth of smaller cells. It need only be sufficiently impermeable in this use to seal the reproductive lumen sufficiently to effect contraception.

The stent-like occluding component 11 will usually have an open walled structure and will be permeable enough to allow tissue growth into the interior thereof. The stent-like occluding component 11 has at least one end portion that extends beyond the ends of the balloon-like barrier component 12. The proximal end portion 25 or the distal end portion 26 or both of the stent-like occluding component 11 which extend beyond the barrier component 12 have fibrous members 20 and 21 within them to facilitate and support tissue ingrowth for long term or permanent occlusion of the body lumen. Hooks or barbs 27 are provided on the stent-like occluding component 11 to secure the occluding device within the body lumen 22 when in the expanded configuration as shown in FIG. 1B.

Figure 2A:
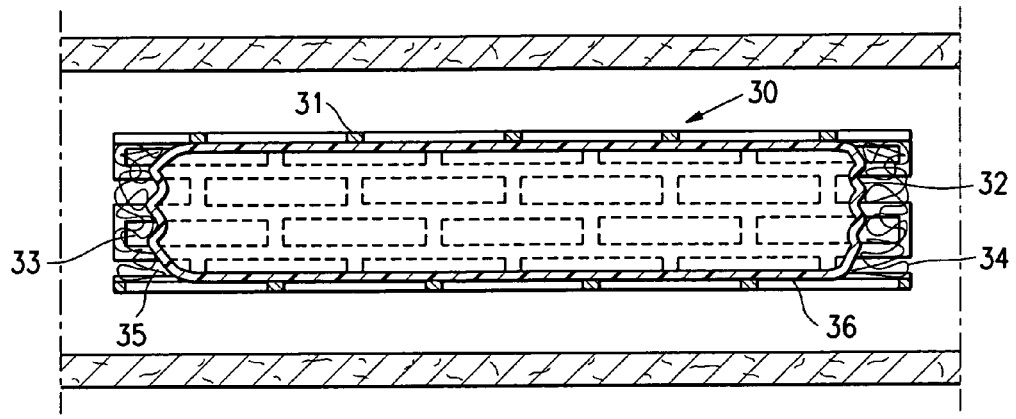
FIG. 2A is a longitudinal cross sectional view of an alternative occluding device embodying features of the invention wherein an impermeable sack is disposed within the interior of the occluding component which is shown in an unexpanded configuration.
Figure 2B:
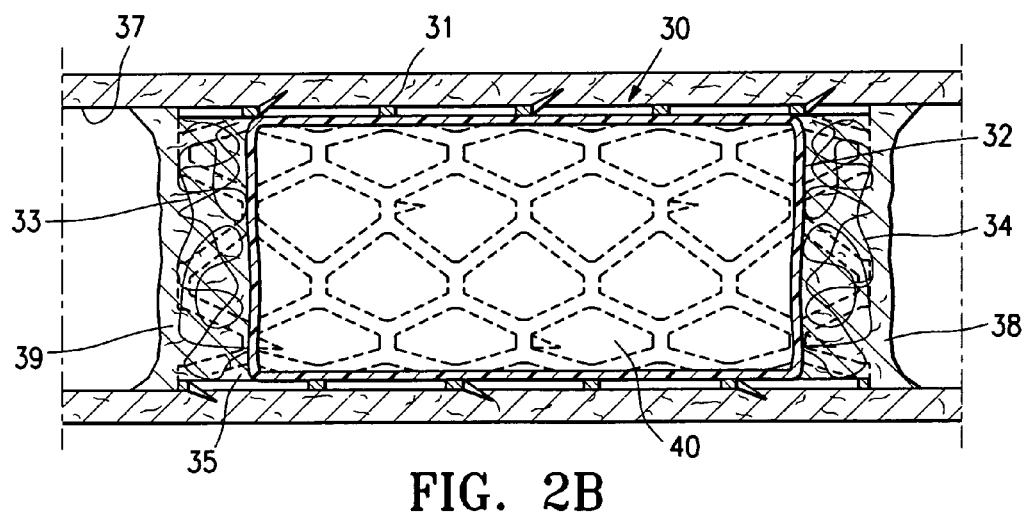
FIG. 2B is a longitudinal cross sectional view of the occluding device shown in FIG. 2A with the device in an expanded configuration and with tissue ingrowth about the occluding component, taken along the lines 2B-2B in FIG. 2A.

FIGS. 2A and 2B illustrate an alternative occluding device 30 which has a self-expanding stent-like occluding component 31, an impermeable barrier component 32 and one or more fibrous permeable components 33 and 34 disposed within the inner lumen 35 of the occluding component. The impermeable barrier component 32 is an impermeable membrane sack 36 loosely contained within the inner lumen 35 of the stent-like occluding component 31. The occluding device 30 is delivered to a desired location within a patient's body lumen 37 and released as previously described. The stent-like occluding component 31 self expands as depicted in FIG. 2B, for example if it is formed of a heat memory metal that expands to the larger diameter configuration when it reaches body temperature or it self expands due to a phase change from stress induced or stress maintained martensite to austenite upon release of the stress resulting in expansion. The occluding component expands so that it is in contact with the luminal walls of the body lumen 37 and simultaneously expands the membrane sack 36 within it which forms the barrier component 32. The membrane sack 36 may be secured to the wall of the occluding component 31 and expand when the occluding component expands. Alternatively, the membrane sack 36 may be biased to expand, for example, by the presence of compressed gas within the interior 40 of the membrane sack, so that when the stent like structure expands when released from the delivery catheter, the barrier component expands to its larger diameter configuration to provide an impermeable barrier across the inner lumen 35 of the occluding component 31. One or more fibrous bodies 33 and 34 are provided in the ends of the occluding component 31 to facilitate and enhance tissue ingrowth therein. Tissue ingrowth 38 and 39 occurs over time around and through the perimeter of the occluding component 31 including the ends, forming a permanent barrier to the passage of biological components. If the membrane sack is formed of a material that causes irritation or otherwise stimulates a tissue ingrowth response, e.g. PET, the tissue ingrowth may be enhanced or accelerated.

Figure 3A:
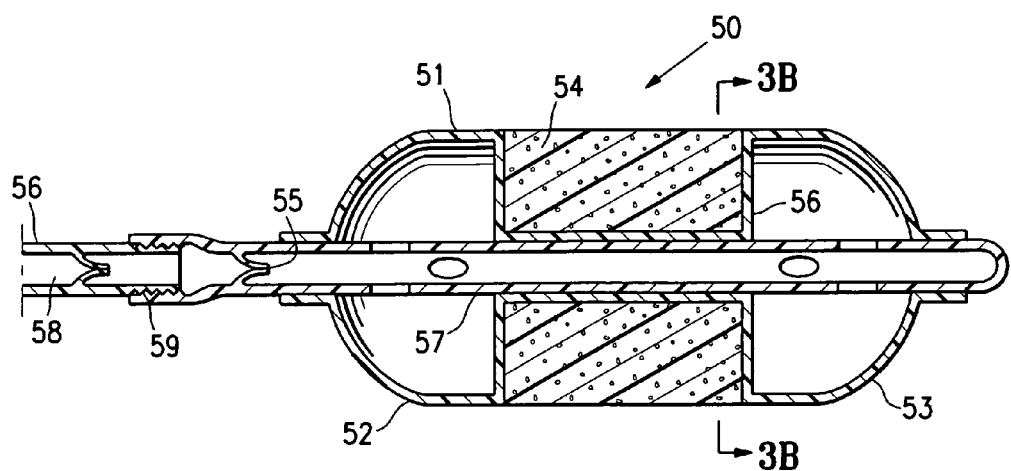
FIG. 3A is a longitudinal center-line cross sectional view of an alternative occluding device embodying features of the invention with a detachable occluding component with inflatable segments.
Figure 3B:
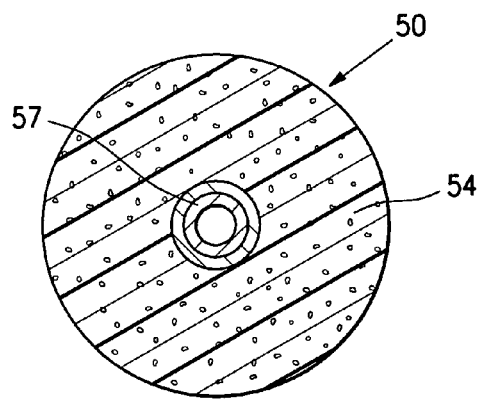
FIG. 3B is a transverse cross-sectional view of the occluding device shown in FIG. 3A.

FIGS. 3A and 3B illustrate an alternative occluding member 50 embodying features of the invention which has an occluding component 51 comprising inflatable impermeable segments 52 and 53 and one intermediate permeable component 54 disposed between the impermeable segments. The inflatable impermeable end segments 52 and 53 of the occluding component may be formed of impermeable material such as polyethylene terephthalate (PET), silicone rubber and other impermeable biocompatible polymeric materials. The permeable intermediate section 54 may be made of compressible open celled foam. The balloon segments 52 and 53 may be separated from the foamed intermediate section 54 by impermeable sectioning walls 55 and 56. An inflation tube 57 passes through the intermediate section 54 and connects the two inflatable segments 52 and 53 so that when an inflation fluid, such as saline, contrast fluid or a biocompatible gas, is introduced down the catheter lumen 58, it will inflate both segments 52 and 53. Forming the inflatable segments 52 and 53 of a relatively non-compliant polymeric material such as PET allows the size and form of the inflatable portions 52 and 53 to be predetermined, for example as a dumb bell shape with the intermediate foam segment 54 between the two large segments. Bio-absorbable material materials may be used for the inflatable segments, but the rate of bio-absorption should be sufficiently slow so that the these segments which form an impermeable barrier component will not be absorbed prior to effective sealing of the body lumen by tissue ingrowth.

The occluding device 50 is releasably attached to the distal shaft section of delivery catheter (not shown) in a similar manner to that shown in FIGS. 1A-1B. A one-way duck-billed inflation valve 55 is provided, as in the previous example, to maintain the inflated segments of the occluding component 51 inflated when the component 51 is detached from the delivery catheter. The permeable intermediate foam segment 54 may be formed of suitable biocompatible polymeric material that will form a support matrix for and enhance tissue ingrowth. For example, the intermediate foam segment 54 may be formed of open celled foam into and through which tissue ingrowth can occur.

In use, the compressible occluding device 50 will be compressed to fit within the inner lumen of a delivery sheath (not shown). The occluding device 50 may be constrained within a stent-like tubular structure (not illustrated) or may be a free-standing device. When the occluding device 50 has been advanced to the desired place in the patient's body lumen, e.g. a fallopian tube and discharged the intermediate foam segment 54 usually expands because there is no further constraints and the segment is biased to expand. Inflation fluid is injected into the interior of the inflatable segments 52 and 53 of the occluding component 51 through the inner lumen of tubular member 57. Likewise, the inflatable end segments 53 and 54 of the occluding component 51 will generally be inflated to essentially the same diameter or a slightly larger diameter of the body lumen so that the exterior surface of the occluding component segments 52 and 53 are snugly pressed against the lumen wall defining the body lumen. The expansion of the intermediate, foam segment 54 may be assisted by the inflation of the end segments 52 and 53, if these inflatable end segments are attached to the ends of the intermediate foam segment 54.

Once the inflatable end segments are inflated within a body lumen (not shown), the distal shaft section 55 of the delivery catheter 56 is detached from the occluding device 50 by rotating the distal shaft section 55 counter clockwise to undo the threaded connection 59 therebetween and then withdrawn the delivery catheter 56. The one way valve 55 prevents inflation fluid within the end segments 52 and 53 from escaping and helps maintain the inflated end segments in their inflated configuration. Because the impermeable end segments 52 and 53 are pressed snugly against the body lumen wall, an effective occlusion of the body lumen occurs that is immediately effective and continues to be an effective barrier until tissue growth into and onto the occluding component 51 effectively occludes and seals the body lumen. By the time the tissue of the body lumen is capable of regrowing and reorganizing to form a bypass around the obstruction (i.e. recannalize), tissue ingrowth into the foam section has formed a permanent occlusion and the body lumen has been effectively and permanently sealed.

For example, if this device were placed in a fallopian tube, the balloon segments would form an immediate occlusion to prevent the passage of egg cells down the fallopian tube or sperm cells up the fallopian tube, effectively providing immediate contraception by the impermeable balloon in the fallopian tube. By the time the fallopian tube could form a new channel around the balloon structures, a process that might take several weeks to several months, tissue ingrowth into the open celled foam of the permeable component 54 between the impermeable segments 52 and 53 would permanently seal the fallopian tube, thus providing permanent contraception.

Figure 4:
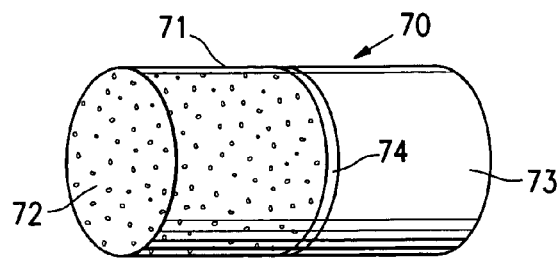
FIG. 4 is a perspective view of an alternative occluding device embodying features of the invention having impermeable and permeable components forming part of the occluding component.

FIG. 4 illustrates in another occluding device 70 embodying features of the invention in which the occluding component 71 is in the form of an elongated plug 72. The occluding component 71 has a plurality of segments 72 and 73, at least one of which is permeable and one of which is impermeable. Permeable segment 72 is formed of permeable open celled polymeric foam which facilitates tissue ingrowth. Impermeable segment 73 is formed of impermeable closed cell polymeric foam. Preferably, an impermeable membrane 74 is provided between the permeable and impermeable segments 72 and 73.

Figure 9A:
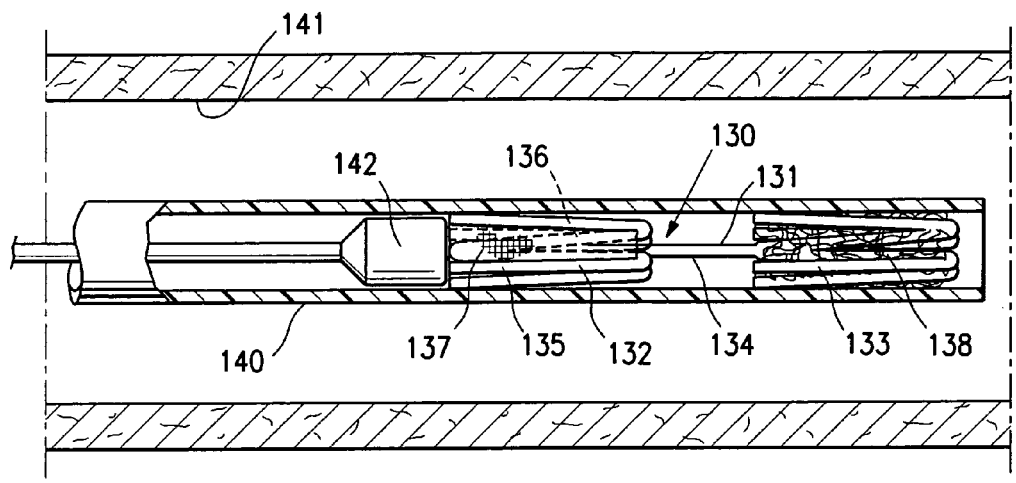
FIG. 9A is an elevational view, partially in section, of another alternative occluding device embodying features of the invention with the occluding device contained within the lumen of a delivery tube.

Essentially the entire occluding component 71 is compressible to facilitate delivery within a delivery sheath (not shown, but see FIGS. 7A and 9A) and is biased to expand when released for deployment within desired location of the body lumen. The expanded deployed configuration is preferably of sufficient size to press against the wall of the lumen to secure the plug 72 in the body lumen.

The segments 72 and 73 may be separated by an impermeable membrane 74, or may be merely formed in alternating sections. At least one segment will generally be permeable to support cell ingrowth, and at least one segment will generally be impermeable to form an immediately effective barrier to cellular migration through the body lumen, although only the membrane may be impermeable and may form the impermeable barrier.

Figure 5:
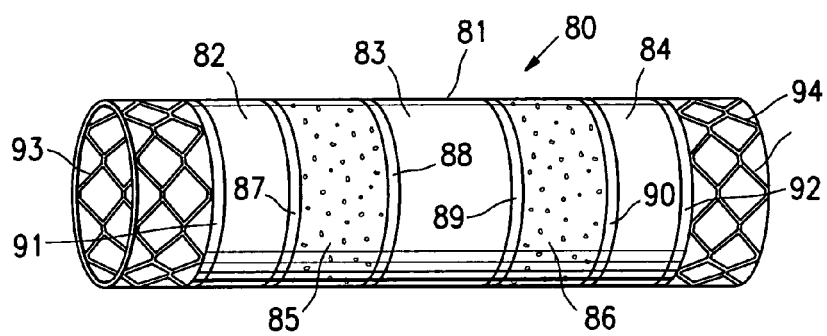
FIG. 5 is a perspective view of another alternative occluding device embodying features of the invention wherein the occluding component has a plurality of permeable and impermeable components and stent-like attachment rings at each end.

FIG. 5 illustrates another alternative embodiment of an occluding device 80 having features of the invention which include an occluding component 81, a plurality of impermeable barrier components 82, 83 and 84 and a plurality of permeable components 85 and 86 for facilitating tissue ingrowth. Preferably, impermeable membranes 87, 88, 89 and 90 are provided between adjacent permeable and impermeable components. Impermeable membranes 91 and 92 are preferably provided on the ends of the occluding component. Short stent like attachment rings 93 and 94 may be provided at the ends of the occluding component to help anchor the component within the body lumen it is deployed and resist expulsion, e.g. by the sweeping of the cilia of a fallopian tube. The attachment rings 93 and 94 may have hooks or barbs (not shown) to more firmly secure the device 80 within a body lumen. The attachment rings 93 and 94 may also support tissue ingrowth to further seal the occluding device 80 within the body lumen. The occluding device 80 may be deployed in a manner similar to that described above for the embodiment shown in FIG. 4.

Figure 6A:
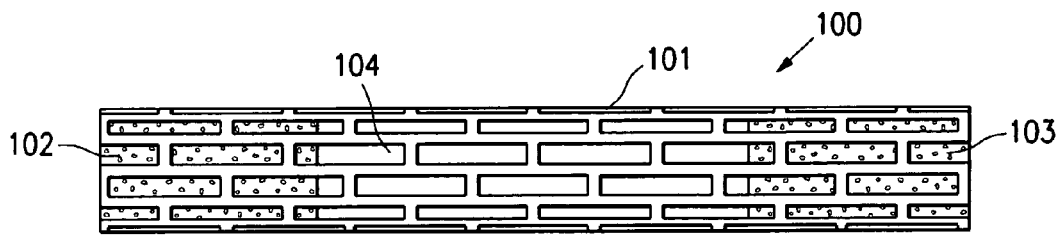
FIG. 6A is an elevational view of another alternative occluding device embodying features of the invention with porous plugs disposed within the occluding component in an unexpanded configuration.
Figure 6B:
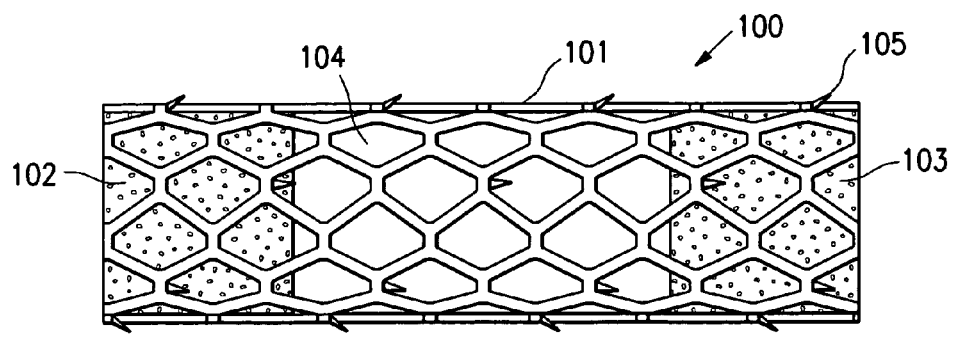
FIG. 6B is an elevational view of the occluding device shown in FIG. 6A in an expanded configuration.

A further alternative embodiment is depicted in FIGS. 6A and 6B. In this embodiment the occluding device 100 comprises a stent-like occluding component 101 with foam plugs 102 and 103 disposed within the inner lumen 104 of the occluding component 101 at each end. The foam plugs 102 and 103 are formed of suitable foamed polymeric material that is sufficiently porous to facilitate tissue ingrowth but is of sufficient length to act as an impermeable barrier to preclude passage of undesirable biological components when deployed within the patient's body lumen. Alternatively, one foam plug may be formed of permeable open cell foam and one foam plug may be formed of impermeable closed cell foam. The individual plugs 102 and 103 may also have one section formed of permeable open cell foam and one section formed of impermeable closed cell foam as shown in FIG. 4 FIG. 6A illustrates the occluding device 100 in the unexpanded configuration and FIG. 6B illustrates the device in the expanded configuration. The foam plugs 102 and 103 are sufficiently flexible so as to expand with the stent like occluding component 101 or be biased to expand with the occluding component. The stent-like occluding component 101 may have barbs 105 to secure the occluding component within the body lumen.

Figure 7A:
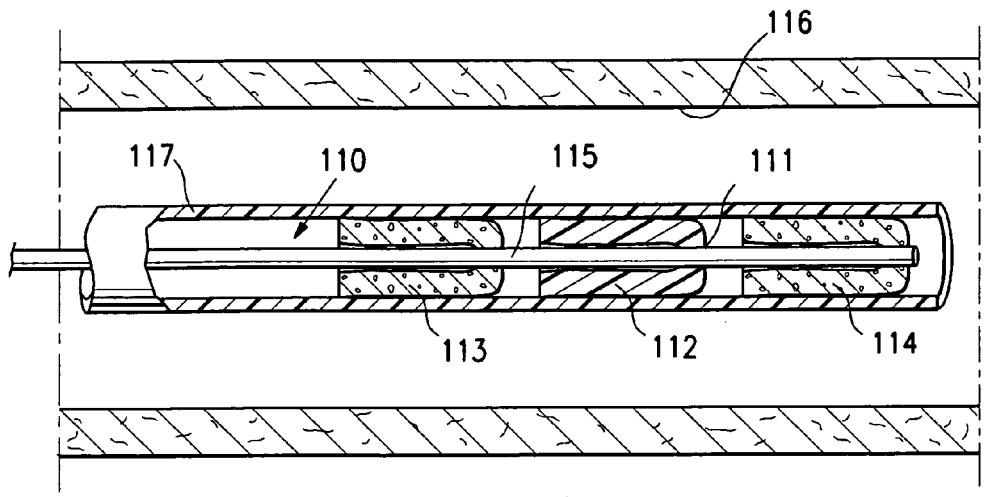
FIG. 7A is an elevational view of another alternative occluding device disposed within a delivery tube with impermeable barrier components and permeable components in the form of unexpanded disks.
Figure 7B:
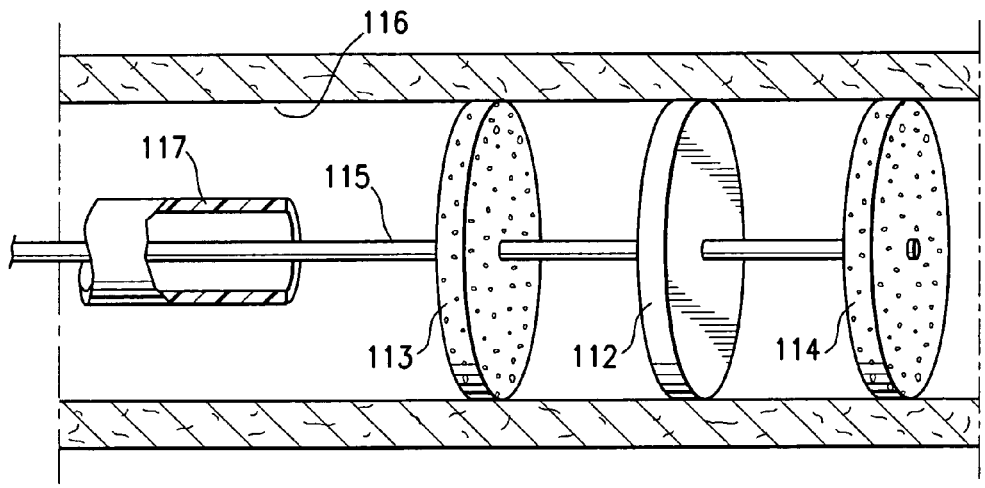
FIG. 7B is an elevational view, partially in section, with the occluding device extending out of the delivery tube and the impermeable barrier component and the permeable components in expanded configuration.

An additional alternative occluding device 110 having features of the invention is depicted in FIGS. 7A and 7B, wherein the device 110 has an occluding component 111, an impermeable barrier component 112 for an immediate occluding of the body lumen and permeable components 113 and 114 to facilitate tissue ingrowth as described above for a permanent occlusion. The impermeable barrier component 112 is in the form of a disk and is secured to a central shaft 115. They may be formed of impermeable closed cell polymeric material. The permeable components 113 and 114 are secured to the shaft 115 and are in the form of a disk formed of an open celled polymeric material. The occluding device 110 may be inserted into the body lumen 116 with the disks in a compressed configuration (FIG. 7A) within the lumen of a delivery sheath 117. When the disks are located at the desired place in the body lumen, the shaft 115 is held in place and the delivery sheath 117 is withdrawn. Upon discharge, the disks 112-114 expand into secure contact with the wall defining the body lumen 116 as shown in FIG. 7B.

While not shown in FIGS. 7A and 7B, the proximal portion of the support shaft 115 may have a threaded releasable attachment such as the threaded connection shown in FIGS. 1A-1B to allow for release of the occluding device 110 by rotating the proximal portion of the support shaft 115. This configuration has the added advantage of allowing the shaft 115 to be used initially to load the occluding device by pulling it into the lumen of a delivery sheath, e.g. through a funnel, and subsequently deploying the occluding device by holding the device in place while the delivery sheath 117 is withdrawn.

Impermeable disk 112 effects an immediate barrier to the passage of undesirable biological components such as eggs and sperm cells and permeable disks 113 and 114 facilitate tissue ingrowth for permanent occlusion. The disks forming the occluding device 110 should have sufficient length to diameter aspect ratios to create a slightly cylindrical shape to enhance the placement and ensure that the disks do not rotate into a flat position that would not effectively seal the body lumen.

Figure 8:
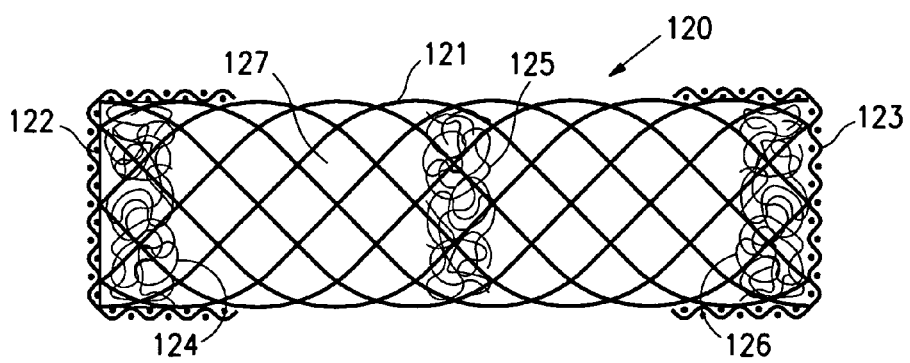
FIG. 8 is an elevational view of an occluding device embodying features of the invention where the occluding component is in the form of a stent-like structure, impermeable components are on both ends of the stent-like occluding component and permeable components in the form of fibrous masses are within the inner lumen of the stent-like occluding component.

FIG. 8 illustrates yet another embodiment which has features of the invention. Specifically, the occluding device 120 has a stent-like occluding component 121 similar to that shown in FIGS. 1A-1C, impermeable barrier components 122 and 123 in the form of impermeable membranes on each end of the occluding component. Permeable components 124, 125 and 126 in the form of fibrous masses are disposed within the inner lumen 127 of the occluding component 121. The permeable components encourage tissue ingrowth as in the previous embodiments. The impermeable barrier component 122 and 123 may be stretched over the ends the expandable stent-like structure 121 to provide for an immediate effective seal of a body lumen when the occluding component 121 is expanded within the body lumen. The permeable components 124-126 are preferably secured within the inner lumen 127 and configured to expand with the wall of the occluding component 121 when it is expanded during deployment at the desired site.

Figure 9B:
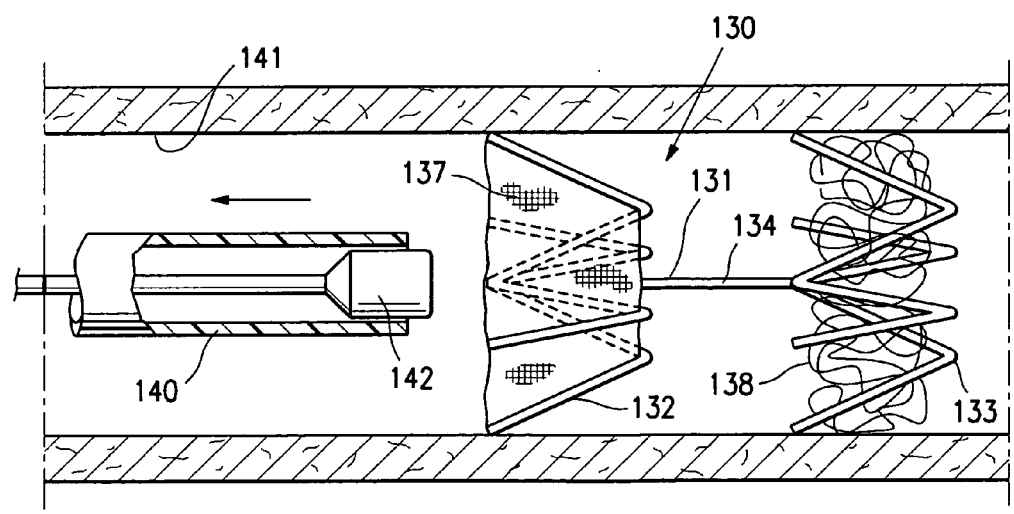
FIG. 9B is an elevational view, partially in section, of the occluding device shown in FIG. 9A deployed within a body lumen in an expanded configuration.

FIGS. 11A and 11B illustrate an alternative occluding device 130 which is similar to the occluding device described in co-pending application Ser. No. 10/746,131, filed on Dec. 24, 2004. The device 130 comprises an occluding component 131 which has spider-like expandable elements 132 and 133 secured to a central shaft 134. The spider-like elements 132 and 133 each have a plurality of legs which extend out from the shaft 134 and which have first leg sections 135 and second leg sections 136. An impermeable membrane 137 is secured to one side of the spider-like element 132 which is secured to the legs of spider-like element 132 in the nature of the fabric of an umbrella secured to the ribs thereof. Spider-like expandable element 133 is provided with a fibrous mass 138 similar to the fibrous masses shown in FIG. 8. The occluding device 130 is shown in a retracted configuration in FIG. 9A within a delivery sheath 140 to facilitate advancement and deployment within the patient's body lumen 141. At the deployment site within the body lumen 141, the plunger 142 is held in place while the delivery sheath 140 is withdrawn to discharge the occluding device 130 from the sheath 140. When deployed within the patient's body lumen 141, as shown in FIG. 9B, the spider-like elements 132 and 133 of the occluding component 131 expand to engage the inner surface of the body lumen 141. Upon expansion of the spider-like element 132, the expanded legs thereof stretch the impermeable membrane 137 across the body lumen 141 to provide immediate effective sealing of the body lumen. The fibrous mass 138 within the spider-like element 133 acts to enhance tissue growth within the occluding component 131 and the permanent occlusion of the body lumen 141. Instead of the permeable fibrous mass 138 within the spider-like element 133, a porous permeable membrane may be secured to the legs of the spider-like element 133 to enhance tissue growth within the occluding component 131. There may be an impermeable membrane on one side of the legs of a spider-like element and a permeable membrane on the other side of the legs.

Figure 10:
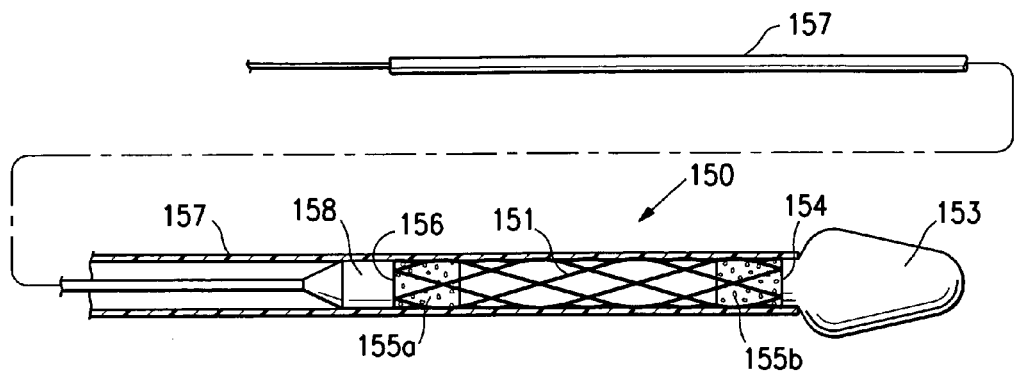
FIG. 10 is an elevational view, partially in section, of an alternative occluding device having features of the invention with an enlarged impermeable barrier component on the distal end of the occluding component.
Figure 11:
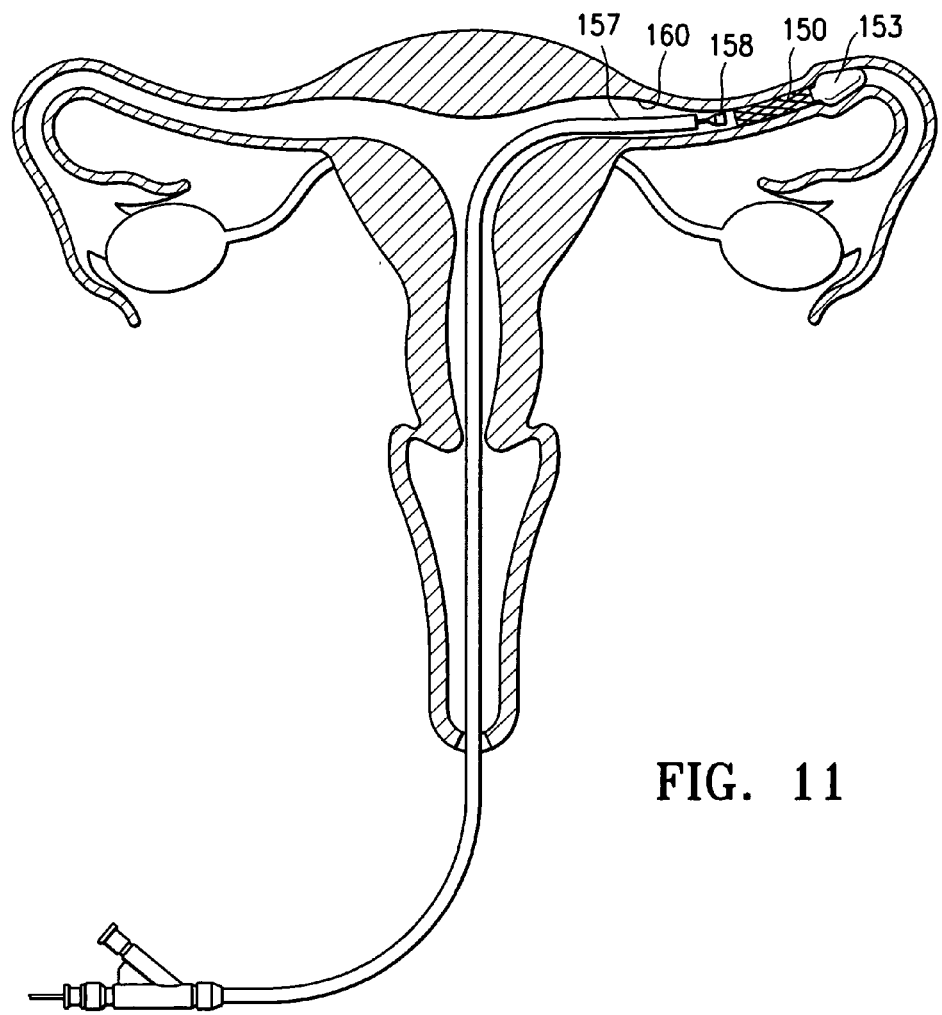
FIG. 11 is a schematic view of the occluding device shown in FIG. 10 disposed within a fallopian tube of a human female.

Another embodiment of an effective occluding device 150 having features of the present invention is shown in FIGS. 10 and 11. The occluding device 150. has an occluding component 151 which includes a stent-like structure 152, a bulbous, bullet-shaped impermeable component 153 secured to the distal end 154 of the stent like structure 152 which is generally slightly larger than the body lumen to be occluded. Permeable components 155a and 155b in the form of porous polymeric masses or bundles are provided within the distal end 154 and the proximal end 156 of the stent-like structure 152. As shown in FIG. 10, the occluding device 150 is partially disposed within a delivery sheath 157 with the enlarged impermeable component 153 extending out of the catheter. A plunger 158 is slidably disposed within the inner lumen 159 of the delivery sheath, proximal to the occluding device 150 and is configured to hold the occluding device 150 while the delivery sheath 157 is withdrawn to deploy the occluding device into the body lumen.

FIG. 11 illustrates the occluding device 150 shown in FIG. 10 disposed within a female patient's fallopian tube 160 after discharge of the occluding device from the delivery sheath 157. The bulbous structure of the enlarged impermeable barrier component 153 stretches the diameter of the body lumen 160 and immediately seals off the lumen to prevent passage of eggs or sperm cells. Other elements such as barbs or hooks (not shown) may be provided on the occluding component to further secure the occluding device 150 within the fallopian tube 161. The stent-like structure of the occluding component 151 may be self-expanding, and the permeable components 152 and 153 which may be secured within the ends of the occluding component 151 and may expand with the occluding component to extend across the luminal passageway and act to enhance and support tissue ingrowth and thereby provide a permanent occlusion of the lumen 160. The permeable components are shown as porous polymeric masses but they may be fibrous mesh or bundled fibers. While the occluding device 150 is shown deployed within a female patient's fallopian tube, it should be apparent that the occluding device may be employed to occlude the reproductive lumen such as a vas deferens of a male patient.

Figure 12:
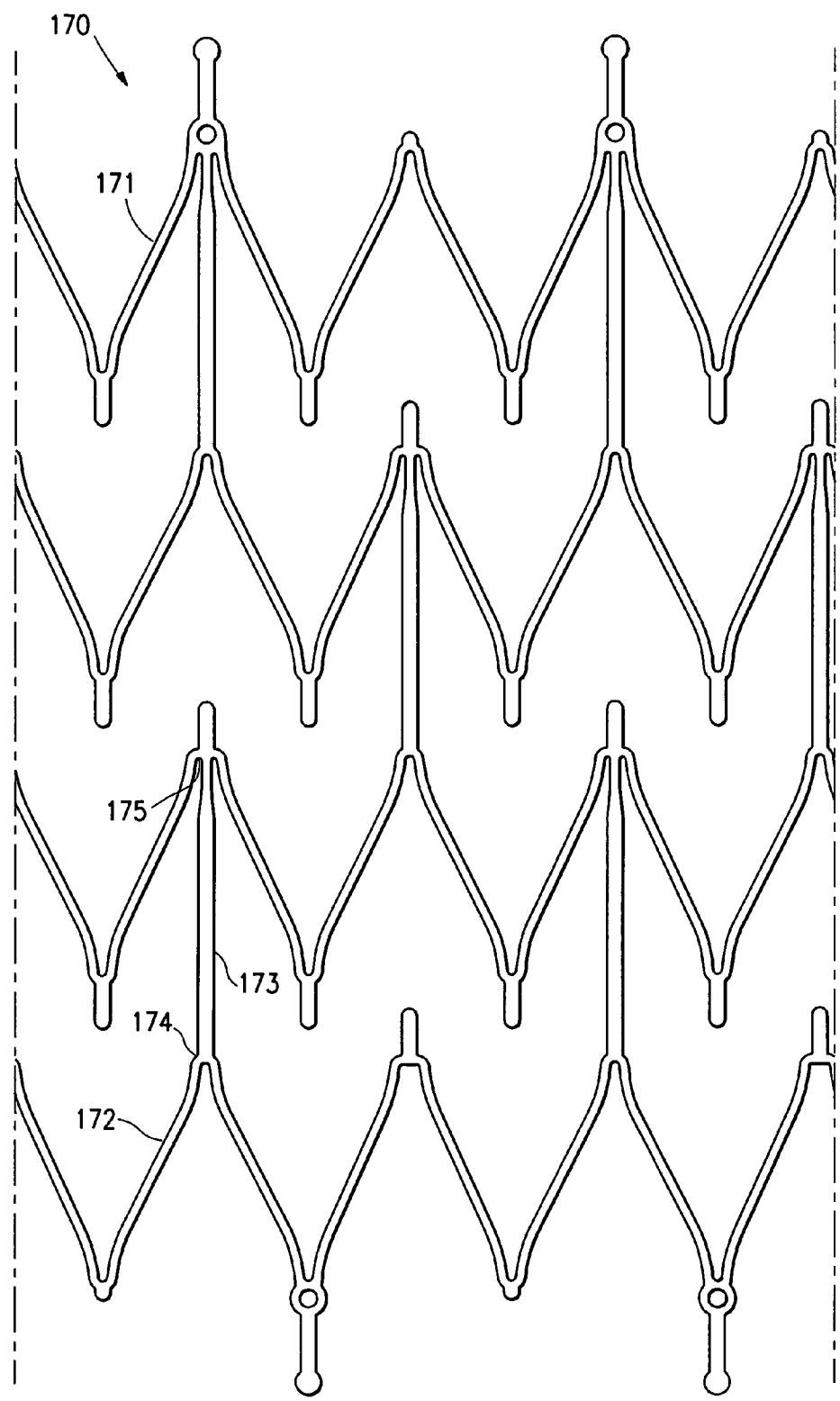
FIG. 12 illustrates detail of a stent-like occluding component that is suitable for use in the present invention.

FIG. 12 illustrates a portion of the wall 170 of a stent-like occluding component 171 which is suitable for use with the present invention. The occluding component 171 has a plurality of interconnected ring sections 172. The ring sections 172 are interconnected by one or more connecting members 173 extending between the peak 174 of an undulation in one ring section to the valley 175 of an adjacent ring section. The adjacent ring sections are off-set or out of phase so that the peaks of one ring section are aligned with the valleys of an adjacent ring section.

The stent-like members described herein can be formed of conventional stent materials including stainless steel, NiTi alloy (shape memory and superelastic), MP35n, Elgiloly and the like. The impermeable materials may be formed of somewhat compliant to essentially non-compliant biocompatible polymeric materials such as PET, nylon Hytrel® and the like. The permeable materials can be fibrous materials such as polyester, nylon, and the like or porous polymeric foam materials impermeable closed cell foam and permeable open cell foam may be formed of expanded polytetraflouroethyene (ePTFE).

Various modifications and improvements may be made to the present invention without departing from the scope thereof. For example, while the invention has been discussed primarily in terms of occluding a reproductive body lumen, the occluding device may be used to occlude a variety of body lumens or passageways. Moreover, although individual features of the invention may be described with respect to one or more of the embodiments but not in other embodiments, those skilled in the art will recognize that individual features of one embodiment of the invention can be combined with any or all the features of one or more of other embodiments.

Terms such as "element", "member", "device", "section", "portion", "component", "means", "step" and words of similar import, when used in the following claims, shall not be construed as invoking the provisions of 35 U.S.C. §112 (6) unless the claims expressly use the term "means" followed by a particular function without specific structure or the term "step" or "steps" followed by a particular function without specific action. The full disclosures of all patents and patent applications referred to are incorporated herein by reference.

What is claimed is:

1. A sterilizing device implantable into a patient's reproductive lumen, comprising:
   an expandable occluding component that is self-expandable upon deployment from a catheter within a patient's reproductive lumen;
   a first barrier component comprising a first membrane that is configured to expand across the reproductive lumen upon self-expansion of the expandable occluding component within the patient's reproductive lumen such that the first membrane is immediately impermeable to the passage of human sperm cells upon deployment of the expandable occluding component;
   a second barrier component comprising a second membrane that is configured to expand across the reproductive lumen upon self-expansion of the expandable occluding component within the patient's reproductive lumen such that the second membrane is immediately impermeable to the passage of human sperm cells upon deployment of the expandable occluding component; and
   at least one fibrous mass that is disposed within one end of the expandable occluding component such that the fibrous mass is permeable and facilitates tissue growth into the expandable occluding component, wherein the fibrous mass is positioned parallel to the first membrane and configured to expand with a wall of the expandable occluding component, and wherein the fibrous mass is made of a foam material;

wherein the expandable occluding component has an elongated tubular shape with first and second ends and an inner lumen extending between the first and second ends, the first membrane is disposed over the first end, and the second membrane is disposed over the second end.

2. The sterilizing device of claim 1 wherein the first membrane is stretched over the first end.

3. The sterilizing device of claim 1 wherein the foam material of the fibrous mass is at least one of a porous polymeric foam material and a permeable open cell foam.

4. The sterilizing device of claim 3 wherein the first barrier component and the second barrier component form a seal of a body lumen when the expandable occluding component is expanded within the body lumen.

5. The sterilizing device of claim 3 wherein the at least one fibrous mass comprises a first fibrous mass within the first end of the expandable occluding component and a second fibrous mass within the second end of the expandable occluding component.

6. The sterilizing device of claim 5 wherein the at least one fibrous mass comprises a third fibrous mass disposed within the inner lumen of the expandable occluding component at an intermediate location between the first and second fibrous masses.

7. The sterilizing device of claim 1 wherein the first membrane is formed of polymeric material.

8. The sterilizing device of claim 1 wherein the expandable occluding component is expandable from a first configuration to a second configuration having a greater transverse cross-sectional dimension than the first configuration.

9. The sterilizing device of claim 1 wherein the first barrier component is bioabsorbable.

10. The sterilizing device of claim 1 wherein the fibrous mass is secured within the inner lumen at an intermediate location between the first and second ends.

* * * * *